United States Patent
Takahashi et al.

(10) Patent No.: US 6,172,265 B1
(45) Date of Patent: Jan. 9, 2001

(54) KETOSUFONE DERIVATIVES AND PROCESS FOR PRODUCING THE SAME

(75) Inventors: Toshiya Takahashi, Ibaraki; Shinzo Seko, Toyonaka, both of (JP)

(73) Assignee: Sumitomo Chemical Company Limited, Osaka (JP)

( * ) Notice: Under 35 U.S.C. 154(b), the term of this patent shall be extended for 0 days.

(21) Appl. No.: 09/332,995

(22) Filed: Jun. 15, 1999

(30) Foreign Application Priority Data

Jun. 18, 1998 (JP) .................................................. 10-171249
Jun. 19, 1998 (JP) .................................................. 10-173157
Jun. 22, 1998 (JP) .................................................. 10-174564

(51) Int. Cl.$^7$ ................................................ C07C 315/04
(52) U.S. Cl. ............................................... 568/31; 568/28
(58) Field of Search ........................................ 568/28, 31

(56) References Cited

U.S. PATENT DOCUMENTS 5,185,468 * 2/1993 Mori et al. ................................. 568/31
5,237,102 * 8/1993 Mori et al. ................................. 568/31

OTHER PUBLICATIONS

CA:88:23202 abs of JP2093748, Aug. 1977.*
CA:88:89888 abs of JP52106846, Sep. 1997.*
CA:88:2289 abs of JP52093750, Aug. 1977.*
CA:84165055 abs of Tetrahedron lett by Ueyama et al (6) pp 443–444, 1976.*
CA:118:81209 abs of JP04279536, Oct. 1992.*
Sigeru Torii et al., "Alicyclic Terpenoids from Cyclocitryl Phenyl Sulfides. VI. Syntheses of β–Ionone Derivatives", *Bulletin of the Chemical Society of Japan*, vol. 51, No. 3. 1978, pp. 949–950.
C. Mercier et al., "Organometallic chemistry in industrial vitamin A and vitamin E synthesis", *Pure & Appl. Chem.*, vol. 66, No. 7, 1994, pp. 1509–1518.

* cited by examiner

*Primary Examiner*—Jean F Vollano
(74) *Attorney, Agent, or Firm*—Sughrue, Mion, Zinn, Macpeak & Seas, PLLC

(57) ABSTRACT

There is provided a ketosulfone derivative represented by the formula (I):

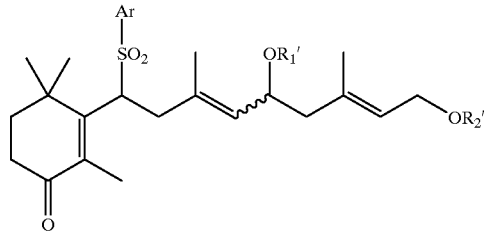

wherein Ar represents an aryl group which may be substituted, and $R_1'$ and $R_2'$ represent a hydrogen atom or a protective group of a hydroxyl group and processes for producing the same.

8 Claims, No Drawings

KETOSUFONE DERIVATIVES AND PROCESS FOR PRODUCING THE SAME

BACKGROUND OF THE INVENTION

1. Field of the Invention

The present invention relates to sulfone derivatives useful in the fields of pharmaceuticals, food and feed additives, and to a process for producing the same.

2. Description of the Related Art

Heretofore, as processes for producing canthaxanthin derivatives and astaxanthin derivatives, a method is known in which a key intermediate, a specific C13 ketone (β-ionone), is subjected to a carbon-increment reaction at its side chain to produce the target compounds via Vitamin A and further β-carotene (Pure Appl. Chem. (1991), 63(1), 35–44). However, β-ionone, which is synthesized via multiple steps, is commercially rather expensive.

SUMMARY OF THE INVENTION

An object of the invention is to provide a process for industrially advantageously producing sulfone derivatives, which are key intermediates for producing canthaxanthin derivatives and astaxanthin derivatives, by oxidizing sulfone compounds derived from inexpensive C10 compounds.

DESCRIPTION OF THE PREFERRED EMBODIMENTS

The present invention provides:

1. A ketosulfone derivative represented by the formula (I):

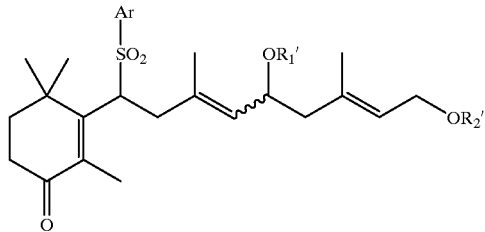

wherein Ar represents an aryl group which may be substituted, and $R_1'$ and $R_2'$ represent a hydrogen atom or a protective group of a hydroxyl group;

2. A process for producing the ketosulfone derivative represented by the formula (I), which comprises reacting a sulfone compound represented by the formula (II):

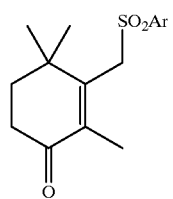

wherein Ar has the same meaning as defined above with a halohydrin derivative represented by the formula (III):

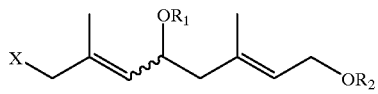

wherein X represents a halogen atom and $R_1$ and $R_2$ represent a protective group of a hydroxyl group, in the presence of a base, optionally followed by removal of the protective group;

3. A process for producing the ketosulfone derivative represented by the formula (I), which comprises reacting a sulfone compound represented by the formula (IV):

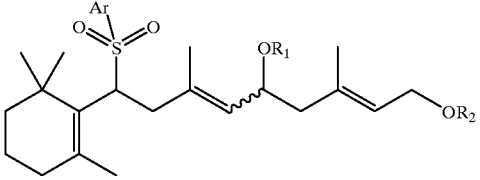

wherein Ar represents an aryl group which may be substituted, and $R_1$ and $R_2$ represent a protective group of a hydroxyl group with an oxidizing agent;

4. A sulfone derivative represented by the formula (V):

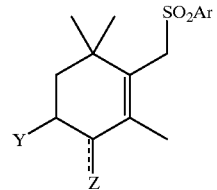

wherein Ar represents an aryl group which may be substituted, Z represents an oxo group (=O) or a hydroxyl group and Y represents a hydrogen atom, a halogen atom or a hydroxyl group; and a process for producing the same.

First, the ketosulfone derivative of the formula (I) will be explained.

$R_1'$ and $R_2'$ in the ketosulfone derivative of the formula (I) represent a hydrogen atom or a protective group of a hydroxyl group. Specific examples of the protective group of the hydroxyl group include acyl groups such as an acetyl group, a pivaloyl group, a benzoyl group and a p-nitrobenzoyl group, silyl groups such as a trimethylsilyl group, a t-butyldimethylsilyl group and a t-butyldiphenylsilyl group, a tetrahydropyranyl group, alkoxymethyl groups such as methoxyethoxymethyl group and a 1-ethoxymethyl group, a benzyl group, a p-methoxybenzyl group, a t-butyl group, a trityl group, a 2,2,2-trichloroethoxycarbonyl group, an allyloxycarbonyl group and so on.

"Ar" in the ketosulfone derivative of the formula (I) represents an optionally substituted aryl group. The aryl group includes a phenyl group, a naphthyl group and the like. Suitable substituents for the aryl groups include C1–C5 alkyl groups such as a methyl group, an ethyl group, a n-propyl group, an isopropyl group, a n-butyl group and a n-pentyl group, C1–C5 alkoxy groups such as a methoxy group, an ethoxy group, a n-propoxy group, a butoxy group and a pentyloxy group, halogen atoms such as a fluorine atom, a chlorine atom, a bromine atom and an iodine atom, and a nitro group, etc.

Specific examples of the optionally substituted aryl group include a phenyl group, a naphthyl group, an o-tolyl group, a m-tolyl group, a p-tolyl group, an o-methoxyphenyl group, a m-methoxyphenyl group, a p-methoxyphenyl group, an o-chlorophenyl group, a m-chlorophenyl group, a p-chlorophenyl group, an o-bromophenyl group, a m-bromophenyl group, a p-bromophenyl group, an o-iodophenyl group, a m-iodophenyl group, a p-iodophenyl group, an o-fluorophenyl group, a m-fluorophenyl group, a p-fluorophenyl group, an o-nitrophenyl group, a m-nitrophenyl group, a p-nitrophenyl group, and the like.

Some ketosulfone derivatives represented by the formula (I) are given in the lowing Table 1.

TABLE 1

Ketosulfone derivatives of the formula (I)

| No. | Ar | $R_1'$ | $R_2'$ |
|---|---|---|---|
| 1 | phenyl | Acetyl | Acetyl |
| 2 | naphthyl | Acetyl | Acetyl |
| 3 | o-tolyl | Acetyl | Acetyl |
| 4 | m-tolyl | Acetyl | Acetyl |
| 5 | p-tolyl | Acetyl | Acetyl |
| 6 | o-methoxyphenyl | Acetyl | Acetyl |
| 7 | m-methoxyphenyl | Acetyl | Acetyl |
| 8 | p-methoxyphenyl | Acetyl | Acetyl |
| 9 | o-chlorophenyl | Acetyl | Acetyl |
| 10 | m-chlorophenyl | Acetyl | Acetyl |
| 11. | p-chlorophenyl | Acetyl | Acetyl |
| 12. | o-bromophenyl | Acetyl | Acetyl |
| 13 | m-bromophenyl | Acetyl | Acetyl |
| 14 | p-bromophenyl | Acetyl | Acetyl |
| 15 | o-iodophenyl | Acetyl | Acetyl |
| 16 | m-iodophenyl | Acetyl | Acetyl |
| 17 | p-iodophenyl | Acetyl | Acetyl |
| 18 | o-fluorophenyl | Acetyl | Acetyl |
| 19 | m-fluorophenyl | Acetyl | Acetyl |
| 20 | p-fluorophenyl | Acetyl | Acetyl |
| 21 | o-nitrophenyl | Acetyl | Acetyl |
| 22 | m-nitrophenyl | Acetyl | Acetyl |
| 23 | p-nitrophenyl | Acetyl | Acetyl |

Further specific examples of ketosulfone derivatives represented by the formula (I) include those compounds having a pivaloyl group, a benzoyl group, a p-nitrobenzoyl group, a trimethylsilyl group, a t-butyldimethylsilyl group, a t-butyldiphenylsilyl group, a tetrahydropyranyl group, a methoxymethyl group, a methoxyethoxymethyl group and a 1-exthoxyethyl group, a benzyl group, a p-methoxybenzyl group, a t-butyl group, a trityl group, a 2,2,2-trichloroethoxycarbonyl group or an allyloxycarbonyl group in place of the acetyl group for $R_1'$ and $R_2'$ in the compound as listed in Table 1. Also those compounds having a hydrogen atom for $R_1'$ and/or $R_2'$ are included in ketosulfone derivative of the formula (I).

The ketosulfone derivative of the formula (I) can be obtained by reacting the sulfone compound of the formula (II) with the halohydrin derivative of the formula (III) wherein $R_1$ and $R_2$ represent a protective group of a hydroxyl group in the presence of a base, and optionally followed by removal of the protective group(s). The removal of the protective group can be carried out in a conventional manner according to "Protective Groups in Organic Synthesis, Greene and Wuts, 2nd Edition (1992), John Wiley & Sons, Inc, the whole disclosure of which is incorporated herein by reference.

X of the halohydrin derivative of the formula (m) may be a halogen atom such as a chlorine atom, a bromine atom and an iodine atom.

Examples of $R_1$ and $R_2$ of the halohydrin derivative (m) include protective groups of a hydroxyl group mentioned in the explanation of $R_1'$ and $R_2'$ of the ketosulfone derivative of the formula (I).

Some halohydrin derivatives represented by the formula (III) are given in the following Table 2.

TABLE 2

Halohydrin derivatives of the formula (III)

| No. | X | R1 | R2 |
|---|---|---|---|
| 1 | Br | Acetyl | Acetyl |
| 2 | Cl | Acetyl | Acetyl |
| 3 | I | Acetyl | Acetyl |

Further specific examples of halohydrin derivatives represented by the formula (I) include those compounds having a pivaloyl group, a benzoyl group, a p-nitrobenzoyl group, a trimethylsilyl group, a t-butyldimethylsilyl group, a t-butyldiphenylsilyl group, a tetrahydropyranyl group, a methoxymethyl group, a methoxyethoxymethyl group and a 1-ethoxyethyl group, a benzyl group, a p-methoxybenzyl group, a t-butyl group, a trityl group, a 2,2,2-trichloroethoxycarbonyl group or an allyloxycarbonyl group in place of the acetyl group for $R_1$ and/or $R_2$ in the compound as listed in Table 2.

Examples of the base used in the reaction include alkyllithiums, Grignard reagents, hydroxides of alkaline metals, hydroxides of alkaline earth metals, hydrides of alkali metals, hydrides of alkaline earth metals, alkoxides of alkali metals, alkoxides of alkaline earth metals, etc. Specific examples of the base include n-butyllithium, s-butyllithium, t-butyllithium, ethylmagnesium bromide, ethylmagnesium chloride, sodium hydroxide, potassium hydroxide, sodium hydride, potassium hydride, sodium methoxide, potassium methoxide, potassium t-butoxide, sodium t-butoxide, and the like.

The amount of the base used is usually about 0.1 to 2 mol per mol of the sulfone compound (II).

In some cases, a phase transfer catalyst is preferably employed in the reaction in order to accelerate the reaction.

Examples of the phase transfer catalyst include quaternary ammonium salts, quaternary phosphonium salts and sulfonium salts.

Examples of the quaternary ammonium salts include ammonium halides having an alkyl group having 1 to 24 carbon atoms and/or an aryl group such as tetramethylammonium chloride, tetraethylammonium chloride, tetrapropylammonium chloride, tetrabutylammonium chloride, tetrapentylammonium chloride, tetrahexylammonium chloride, tetraheptylammonium chloride, tetraoctylammonium chloride, tetrahexadecylammonium chloride, tetraoctadecylammonium chloride, benzyltrimethylammonium chloride, benzyltriethylammonium chloride, benzyltributylammonium chloride, 1-methylpyridinium chloride, 1-hexadecylpyridinium chloride, 1,4-dimethylpyridinium chloride, trimethylcyclopropylammonium chloride, tetramethylammonium bromide, tetraethylammonium bromide, tetrapropylammonium bromide, tetrabutylammonium bromide, tetrapentylammonium bromide, tetrahexylammonium bromide, tetraheptylammonium bromide, tetraoctylammonium bromide, tetrahexadecylammonium bromide, tetraoctadecylammonium bromide, benzyltrimethylammonium bromide, benzyltriethylammonium bromide, benzyltributylammonium bromide, 1-methylpyridinium bromide, 1-hexadecylpyridinium bromide, 1,4-dimethylpyridinium bromide, trimethylcyclopropylammonium bromide, tetramethylammonium iodide, tetrabutylammonium iodide, tetraoctylammonium iodide, t-butylethyldimethylammonium iodide, tetradecyltrimethylammonium iodide, hexadecyltrimethylammonium iodide, octadecyltrimethylammonium iodide, benzyltrimethylammonium iodide, benzyltriethylammonium iodide, benzyltributylammonium iodide, etc.

Examples of the quaternary phosphonium salts include tributylmethylphosphonium chloride, triethylmethylphosphonium chloride, methyltriphenoxyphosphonium chloride, butyltriphenylphosphonium chloride, tetrabutylphosphonium chloride, benzyltriphenylphosphonium chloride, hexadecyltrimethylphosphonium chloride, hexadecyltributylphosphonium chloride, hexadecyldimethylethylphosphonium chloride, tetraphenylphosphonium chloride, tributylmethylphosphonium bromide, triethylmethylphophonium bromide, methyltriphenoxyphosphonium bromide, butyltriphenylphosphonium bromide, tetrabutylphosphonium bromide, benzyltriphenylphosphonium bromide, hexadecyltrimethylphosphonium bromide, hexadecyltributylphosphonium bromide, hexadecyldimethylethylphosphonium bromide, tetraphenylphosphonium bromide, tributylmethylphosphonium iodide, triethylmethylphosphonium iodide, methyltriphenoxyphosphonium iodide, butyltriphenylphosphonium iodide, tetrabutylphosphonium iodide, benzyltriphenylphosphonium iodide and hexadecyltrimethylphosphonium iodide, etc.

Examples of the sulfonium salts include dibutylmethylsulfonium chloride, trimethylsulfonium chloride, triethylsulfonium chloride, dibutylmethylsulfonium bromide, trimethylsulfonium bromide, triethylsulfonium bromide, dibutylmethylsulfonium iodide, trimethylsulfonium iodide, triethylsulfonium iodide, etc.

The quaternary ammonium salts are preferred. Especially, the alkyl group having 1 to 24 carbon atoms and/or aryl ammonium halides are preferred.

The amount of the phase transfer catalyst is usually 0.01 to 0.2 mol, preferably 0.02 to 0.1 mol, per mol of the sulfone compound (II).

The reaction is usually carried out in an organic solvent, examples thereof including ether solvents such as diethyl ether, tetrahydrofuran and anisole, hydrocarbon solvents such as n-hexane, n-heptane, cyclohexane, n-pentane, toluene and xylene, halogenated solvents such as chloroform, dichloromethane, 1,2-dichloroethane, monochlorobenzene and o-dichlorobenzene, or aprotic polar solvents such as N,N-dimethylformamide, dimethyl sulfoxide, N,N-dimethylacetamide and hexamethylphosphoric triamide.

The reaction temperature usually falls within the range of from −78° C. up to the boiling point of the solvent to be used.

After the reaction, the ketosulfone derivative (I) can be isolated by a conventional post-treatment, and may be further purified by silica gel chromatography, if necessary.

The halohydrin derivative (III) may be a geometrical isomer such as E-isomer, or Z-isomer or the mixture thereof. Additionally, they may be either racemic or optically active substances.

The sulfone compound (II) used in the present invention can be obtained by reacting the sulfone compound (V-1) described below with an oxidizing agent containing a metal selected from Group 6 and 7 of the Periodic Table of Elements as described below.

Next, there is described the process for producing the ketosulfone derivative of the formula (I) comprising reacting the sulfone derivative (IV) with an oxidizing agent.

In the sulfone derivative of the formula (IV), Ar, $R_1$ and $R_2$ respectively represent the same substituents as those described above for the compounds of the formula (II) and formula (III).

Examples of the oxidizing agent used in the above reaction include salts and oxides of metal including chromium and manganese. Specific examples include pyridinium chlorochromate, pyridinium dichromate, manganese dioxide, etc.

The amount of the oxidizing agent used is usually about 1 to 3 mol per mol of the sulfone derivative (IV).

The reaction is usually carried out in a solvent, examples thereof including aprotic polar solvents such as N,N-dimethylformamide, dimethyl sulfoxide, N,N-dimethylacetamide and hexamethylphosphoric triamide, hydrocarbon solvents such as n-hexane, n-heptane, cyclohexane, n-pentane, toluene and xylene, and halogenated solvents such as chloroform, dichloromethane, 1,2-dichloroethane, monochlorobenzene and o-dichlorobenzene.

The reaction temperature usually falls within the range of from 0° C. up to the boiling point of the solvent to be used.

After the reaction, performing a conventional post-treatment can provide the ketosulfone derivative (I).

The product may be purified by silica gel chromatography, if necessary. The starting material, sulfone derivatives (IV), may be a geometrical isomer such as E-isomer or Z-isomer or the mixture thereof. Additionally, they may be either racemic or optically active substances.

The sulfone derivative (IV), which is the starting compound of the present invention, can be obtained in the form of a compound having a protected hydroxyl group by reacting the sulfone compound of the formula (V-1):

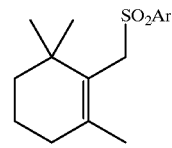

(V-1)

wherein Ar has the same meaning as previously defined with the halohydrin derivative of the formula (III):

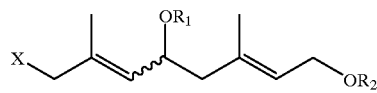

(III)

wherein X represents a halogen atom, and $R_1$ and $R_2$ represent a protective group of a hydroxyl group, in the presence of a base.

Examples of the halogen atom represented by X of the halohydrin derivative (III) include a chlorine atom, a bromine atom, an iodine atom, etc.

Examples of the base used in the reaction include alkyllithiums, Grignard reagents, hydroxides of alkali metals, hydroxides of alkaline earth metals, hydrides of alkali metals, hydrides of alkaline earth metals, alkoxides of alkali metals, alkoxides of alkaline earth metals, etc. Specific examples of the base include n-butyllithium, s-butyllithium, t-butyllithium, ethylmagnesium bromide, ethylmagnesium chloride, sodium hydroxide, potassium hydroxide, sodium hydride, potassium hydride, sodium methoxide, potassium methoxide, potassium t-butoxide, sodium t-butoxide and the like. The amount of the base used is usually about 0.1 to 2 mols per mol of the sulfone compound (V-1).

In some cases, a phase transfer catalyst is preferably employed in the reaction in order to accelerate the reaction.

Examples of the phase transfer catalyst include quaternary ammonium salts, quaternary phosphonium salts, sulfonium salts and the like, which are the same as those used for the reaction of the compounds (III) and (II)

The amount of the phase transfer catalyst used is usually about 0.01 to 0.2 mol, preferably about 0.02 to 0.1 mol, per mol of the sulfone compound (V-1).

The reaction is usually carried out in an organic solvent, examples thereof including ether solvents such as diethyl ether, tetrahydrofuran and anisole, hydrocarbon solvents such as n-hexane, n-heptane, cyclohexane, n-pentane, toluene and xylene, halogenated solvents such as chloroform, dichloromethane, 1,2-dichloroethane, monochlorobenzene and o-dichlorobenzene, and aprotic polar solvents such as N,N-dimethylformamide, dimethyl sulfoxide, N,N-dimethylacetamide and hexamethylphosphoric triamide.

The reaction temperature usually falls within the range of from −78° C. up to the boiling point of the solvent to be used. The reaction time usually falls within the range of from 1 to 24 hours, but varies depending upon the types of the base and catalyst to be used and the reaction temperature.

After the reaction, performing a conventional post-treatment can provide the sulfone derivative (IV).

The product may be purified by silica gel chromatography or the like, if desired.

The starting material, halohydrin derivatives (III), may be the E-geometrical isomers, the Z-geometrical isomers or the mixture thereof. Additionally, they may be either racemic or optically active compounds.

The sulfone compounds (V-1) and the halohydrin derivatives (III) can be synthesized from geraniol or linalool by a method as described below.

The sulfone derivative represented by the formula (V) and a process for producing the same are described below.

Examples of the optionally substituted aryl group in the sulfone derivative (V) include those mentioned above.

The compound wherein, in the formula (V), Z is an oxo group and Y is a hydrogen atom, namely the ketosulfone derivative represented by the formula (V-2):

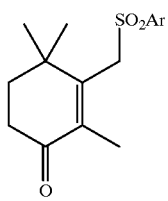

(V-2)

wherein Ar represents an aryl group which may have a substituent can be obtained by reacting the sulfone derivative represented by the formula (V-1):

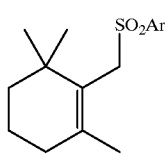

(V-1)

wherein Ar has the same meaning as previously defined with an oxidizing agent containing a metal selected from Group 6 and 7 of the Periodic Table of Elements.

Examples of the oxidizing agent containing a metal selected from Group 6 and 7 of the Periodic Table of Elements include oxides and salts thereof of chromium or manganese such as chromic acid, pyridinium chlorochromate, pyridinium dichromate, manganese oxide, potassium permanganate and tris(acetonylacetate)manganese(III).

The amount of the oxidizing agent used is usually 1 to 10 mols, preferably 1 to 3 mols, per mol of the sulfone derivative (V-1).

The reaction is usually carried out in an organic solvent, examples thereof including aprotic polar solvents such as N,N-dimethylformamide, dimethyl sulfoxide, N,N-dimethylacetamide and hexamethylphosphoric triamide, ether solvents such as dioxane and tetrahydrofuran, hydrocarbon solvents such as n-hexane, n-heptane, cyclohexane, n-pentane, toluene and xylene, and halogenated solvents such as chloroform, dichloromethane, 1,2-dichloroethane, monochlorobenzene and o-dichlorobenzene.

The reaction temperature usually falls within the range of from 0° C. up to the boiling point of the solvent to be used.

After the reaction, performing a conventional post-treatment can provide the ketosulfone derivative (V-2), which may be purified by silica gel chromatography, if desired.

The compound wherein, in the formula (V), Z is a hydroxyl group and Y is a hydrogen atom, namely the hydroxysulfone derivative represented by the formula (V-3):

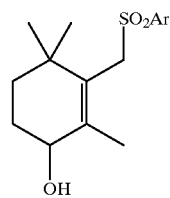

(V-3)

wherein Ar has the same meaning as defined above can be obtained by reacting the sulfone derivative represented by the formula (V-1) with an oxidizing agent containing a metal selected from Group 16 of the Periodic Table of Elements.

Examples of the oxidizing agent containing a metal selected from Group 16 of the Periodic Table of Elements used in the reaction include oxides of selenium such as selenium dioxide The amount of the oxidizing agent used is usually 1 to 10 mols, preferably 1 to 3 mols, per mol of the sulfone derivative (V-1).

The reaction is usually carried out in an organic solvent, examples thereof including aprotic polar solvents such as N,N-dimethylformamide, dimethyl sulfoxide, N,N-dimethylacetamide and hexamethylphosphoric triamide, ether solvents such as dioxane and tetrahydrofuran, hydrocarbon solvents such as n-hexane, n-heptane, cyclohexane, n-pentane, toluene and xylene, and halogenated solvents such as chloroform, dichloromethane, 1,2-dichloroethane, monochlorobenzene and o-dichlorobenzene.

The reaction temperature usually falls within the range of from 0° C. up to the boiling point of the solvent to be used.

After the reaction, performing a conventional post-treatment can provide the hydroxysulfone derivative (V-3) which may be purified by silica gel chromatography, if necessary.

The compound wherein, in the formula (V), Z is an oxo group and Y is a halogen atom, namely the α-haloketosulfone derivative represented by the formula (V-4):

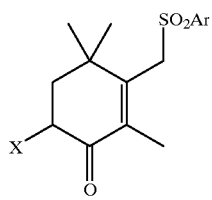

(V-4)

wherein Ar has the same meaning as previously defined and X represents a halogen atom can be obtained by reacting the sulfone derivative represented by the formula (V-1) with an oxidizing agent containing a halogen atom.

Examples of the oxidizing agent containing a halogen atom used in the above reaction include N-halogenated succinimide such as N-bromosuccinimide, N-chlorosuccinimide and N-iodosuccinimide.

The amount of the oxidizing agent containing a halogen atom used is usually 1 to 10 mols, preferably 1 to 3 mols, per mol of the sulfone derivative (V-1).

The reaction is usually carried out in an organic solvent, examples thereof including halogenated solvents such as chloroform, dichloromethane, 1,2-dichloroethane, monochlorobenzene and o-dichlorobenzene, alcohol solvents such as methanol, ethanol and isopropyl alcohol, aprotic polar solvents such as N,N-dimethylformamide, dimethyl sulfoxide, N,N-dimethylacetamide and hexamethylphosphoric triamide, and hydrocarbon solvents such as n-hexane, n-heptane, cyclohexane, n-pentane, toluene and xylene.

The reaction temperature usually falls within the range of from −30° C. up to the boiling point of the solvent to be used.

After the reaction, performing a conventional post-treatment can provide the α-haloketosulfone derivative (V-4) which may be purified by silica gel chromatography, if desired. Examples of α-haloketosulfone derivative (V-4) thus obtained is illustrated in the following Table 3.

TABLE 3

| No. | Ar | X |
|---|---|---|
| 1 | phenyl | Br |
| 2 | naphthyl | Br |
| 3 | o-tolyl | Br |
| 4 | m-tolyl | Br |
| 5 | p-tolyl | Br |
| 6 | o-methoxyphenyl | Br |
| 7 | m-methoxyphenyl | Br |
| 8 | p-methoxyphenyl | Br |
| 9 | o-chlorophenyl | Br |
| 10 | m-chlorophenyl | Br |
| 11. | p-chlorophenyl | Br |
| 12. | o-bromophenyl | Br |
| 13 | m-bromophenyl | Br |
| 14 | p-bromophenyl | Br |
| 15 | o-iodophenyl | Br |
| 16 | m-iodophenyl | Br |
| 17 | p-iodophenyl | Br |
| 18 | o-fluorophenyl | Br |
| 19 | m-fluorophenyl | Br |
| 20 | p-fluorophenyl | Br |
| 21 | o-nitrophenyl | Br |
| 22 | m-nitrophenyl | Br |
| 23 | p-nitrophenyl | Br |

Specific examples of α-haloketosulfone derivative (V-4) further include those compounds having a fluorine, chlorine or iodine atom respectively in place of the bromine atom in the compounds as listed in Table 3.

The compounds wherein, in the formula (IV), Z is an oxo group and Y is a hydroxyl group, namely the α-hydroxyketosulfone derivative represented by the formula (V-5):

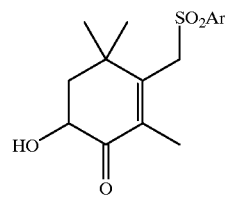

(V-5)

wherein Ar has the same meaning as defined above can be obtained by reacting the foregoing α-haloketosulfone derivative represented by the formula (V-4) with a hydroxide of a metal selected from an alkali metal and an alkaline earth metal Examples of the metal hydroxide include sodium hydroxide, potassium hydroxide and magnesium hydroxide. The amount of the metal hydroxide used is usually 1 to 10 mols, preferably 1 to 3 mols, per mol of the α-haloketosulfone derivative (V-4).

The reaction is usually carried out in an organic solvent, examples thereof including halogenated solvents such as chloroform, dichloromethane, 1,2-dichloroethane, monochlorobenzene and o-dichlorobenzene, alcohol solvents such as methanol, ethanol and isopropyl alcohol, and aprotic polar solvents such as N,N-dimethylformamide, dimethyl sulfoxide, N,N-dimethylacetamide and hexamethylphosphoric triamide.

The reaction temperature usually falls within the range of from 0° C. to the boiling point of the solvent to be used.

After the reaction, α-hydroxyketosulfone derivative (V-5) can be isolated by a conventional post-treatment such as extraction, and evaporation, and may be further purified by silica gel chromatography, if necessary.

The starting compound, namely the sulfone derivative (V-1), can be synthesized from geraniol or linalool.

The sulfone compound (V-1) can be readily synthesized from linalool via a halide compound as described in JP63-250364A and JP63-250363A. The halohydrin derivative (III) can be synthesized from geraniol.

The sulfone derivatives according to the present invention are useful in the fields of pharmaceuticals, food and feed additives, for example as intermediates for producing canthaxanthin derivatives and astaxanthin derivatives.

EXAMPLES

The following Examples further illustrate the present invention in detail, but should not be construed to limit the present invention thereto.

In the Examples, the compounds used are described by reference to symbols provided in FIG. 1.

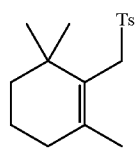

(A)

-continued (B)
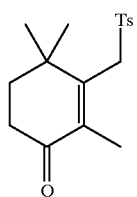

(C)
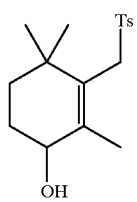

(D)
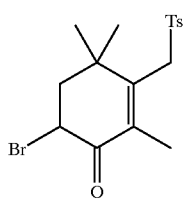

(E)
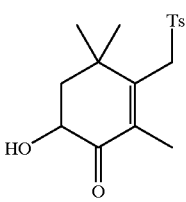

(F)
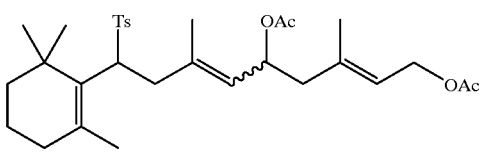

(G)
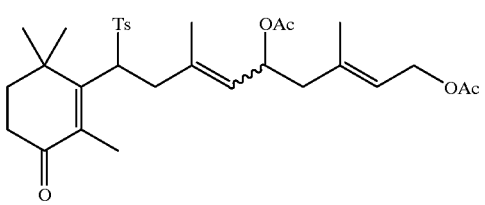

(H)
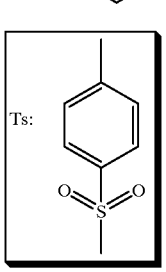

Example 1

0.5 g (1.71 mol) of sulfone (A) was dissolved in 10 ml of dimethyl sulfoxide, and at room temperature to the resulting solution was added dropwise slowly 10 ml of a solution in which 1.13 g (5.13 mmol) of pyridinium chlorochromate was dissolved. The resulting mixture was stirred at that temperature for 3 hours, and then heated up to 50° C. and stirred for 6 hours. After cooling the reaction solution, ether was added to it. The resulting mixture was filtered and washed with water, and then subjected to extraction with ether. A crude product was obtained by distilling the solvent from the organic layer. The crude product was purified by silica gel column chromatography to produce the desired ketosulfone (B) in a yield of 39%.

$^1$H-NMR δ (CDCl$_3$) 1.23 (6H, s), 1.79 (3H, s), 1.90 (2H, t, J=6 Hz), 2.48 (3H, s), 2.55 (2H, t, J=6 Hz), 4.13 (2H, s), 7.33 (2H, d, J=8 Hz), 7.81 (2H, d, J=8 Hz)

$^{13}$C-NMR δ (CDCl$_3$) 13.1, 21.4, 26.9, 34.5, 35.2, 37.3, 58.8, 127.1, 129.4, 137.6, 138.1, 146.0, 150.1, 198.2

Example 2

1.0 g (3.42 mmol) of sulfone (A) was dissolved in 20 ml of 1,4-dioxane, and to the solution was added 0.57 g (5.13 mmol) of selenium dioxide. The reaction solution was heated up to 80° C. and stirred for 1.5 hours. After completion of the reaction, the solid formed was separated by filtration, and a mixture of the desired ketosulfone (B) and hydroxysulfone (C) was obtained by distilling the solvent from the filtrate. The crude product was purified by silica gel chromatography to produce the ketosulfone (B) in a yield of 29% and the hydroxysulfone (C) in a yield of 59%.

$^1$H-NMR δ (CDCl$_3$) 1.00 (3H, s), 1.05 (3H, s), 1.39–1.42 (1H, m), 1.65–1.98 (3H, m), 1.82 (3H, s), 2.44 (3H, s), 3.30 (1H, d, J=8 Hz), 3.98 (3H, m), 7.33 (2H, d, J=8 Hz), 7.81 (2H, d, J=8 Hz)

$^{13}$C-NMR δ (CDCl$_3$) 18.5, 21.4, 27.2, 27.7, 27.9, 28.0, 34.5, 57.8, 69.6, 127.1, 129.4, 138.1, 140.1, 144.2

Example 3

1.0 g (3.42 mmol) of sulfone (A) was dissolved in 5 ml of chloroform and 5 ml of methanol, and to the solution was added 0.61 g (3.42 mmol) of N-bromosuccinimide. The mixture was stirred at room temperature for 18 hours. After confirmation of the disappearance of the starting material by TLC, a crude product was obtained by distilling the solvent from the reaction mixture. The crude product was purified by silica gel column chromatography to produce the desired α-bromoketosulfone (D) in a yield of 37%.

$^1$H-NMR δ (CDCl$_3$) 1.27 (3H, s), 1.30 (3H, s), 1.89 (3H, s), 2.35–2.47 (2H, m), 2.47 (3H, s), 4.08 (1H, d, J=12 Hz), 4.19 (1H, d, J=12 Hz), 4.92 (1H, dd, J=12 Hz, 9 Hz), 7.39 (2H, d, J=8 Hz), 7.81 (2H, d, J=8 Hz)

$^{13}$C-NMR δ (CDCl$_3$) 14.5, 21.4, 26.9, 27.9, 38.5, 48.7, 48.9, 58.8, 127.8, 129.4, 136.9, 138.1, 146.1, 150.2, 190.8

Example 4

0.09 g (0.234 mmol) of α-bromoketosulfone (D) was dissolved in 3 ml of dimethylformamide, and to the solution was added dropwise 0.055 g (0.281 mmol) of a 20% aqueous sodium hydroxide solution. The resulting mixture was stirred at room temperature for 5 hours, and then it was subjected to addition of water and extraction with ether. The organic layer was washed with an aqueous ammonium chloride solution and brine successively. The resulting organic layer was dried over anhydrous magnesium sulfate, and a crude product was then obtained by distilling the solvent from the organic layer. The crude product was purified by silica gel column chromatography to produce the desired α-hydroxyketosulfone (E) in a yield of 77%.

Example 5

0.7 g (1.28 mmol) of the sulfone (F) was dissolved in 25 ml of dimethyl sulfoxide in a flask, and to the resulting solution was added 0.83 g (3.86 mmol) of pyridinium chlorochromate. The resulting mixture was stirred at 50° C. for 10 hours. After completion of the reaction, the reaction mixture was filtered and washed with ether carefully. The filtrate was washed with water and subjected to extraction with ether. The organic layer was dried over anhydrous magnesium sulfate, and a crude product was then obtained by distilling the solvent from the organic layer. The crude product was purified by silica gel column chromatography to isolate the desired ketosulfone (G) as a pale yellow oil in a yield of 41%.

$^{1}$H-NMR δ (CDCl$_3$) 0.88–1.27 (6H, m), 1.39 (3H, s), 1.70 (3H, s), 1.61–1.87 (4H,m), 1.90–2.39(2H, m), 2.00 (3H, s), 2.01 (3H, s), 2.03 (3H, s), 2.44 (3H, s), 2.66–3.11 (2H, m), 3.95–4.12 (1H, m), 4.53 (2H, d, J=7 Hz), 5.10 (1H×40/100, d, J=9 Hz), 5.20 (1H×60/100, d, J=9 Hz), 5.34 (1H, br), 5.45–5.60 (1H, br), 7.33 (2H, d, J=8 Hz), 7.76 (2H, d, J=8 Hz).

$^{13}$C-NMR δ (CDCl$_3$) 15.1, 16.0, 16.1, 16.6, 18.8, 20.8, 20.9, 21.4, 28.2, 29.0, 35.5, 40.5, 40.8, 44.6, 60.8, 65.3, 65.5, 65.7, 68.3, 68.5, 68.8, 121.9, 127.1, 128.3, 129.4, 130.5, 130.6, 136.2, 137.1, 137.6, 137.7, 138.4, 143.9, 144.0, 169.8, 170.0, 170.7, 198

Example 6

0.53 g (1.8 mmol) of the sulfone (B) and 20 ml of THF(tetrahydrofuran) were charged into a flask. After the sulfone was dissolved, the solution was cooled down to −60° C. To the solution was added dropwise slowly 1.13 ml (1.8 mmol) of a n-hexane solution of n-butyllithium at that temperature, and the resulting mixture was kept at that temperature for 3 hours. After this, 5 ml of a THF solution containing 0.3 g (0.9 mmol) of the halohydrin derivative (H) was dropped into the mixture previously obtained in the course of 1 hour. The resulting mixture was stirred at that temperature for 3 hours. After confirmation of the disappearance of one of the starting materials by TLC, the reaction mixture was poured into a saturated aqueous ammonium chloride solution, and then subjected to extraction with ether. The organic layer was washed with a saturated aqueous sodium chloride solution, and then dried over anhydrous magnesium sulfate. A crude product was obtained by distilling the solvent. The crude product was purified by silica gel column chromatography, and the ketosulfone (G) was isolated as a pale yellow oil in a yield of 49%.

What is claimed is:

1. A ketosulfone derivative represented by the formula (I):

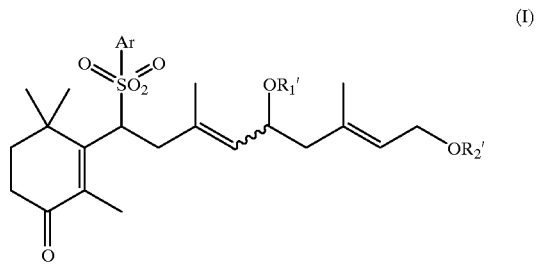

(I)

wherein Ar represents an aryl group which may optionally have a substituent, and $R_1'$ and $R_2'$ represent a hydrogen atom or a protective group of a hydroxyl group.

2. A process for producing the ketosulfone derivative of the formula (I) as defined in claim 1, which comprises reacting a sulfone compound represented by the formula (II):

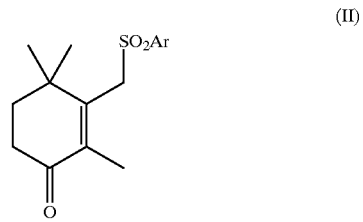

(II)

wherein Ar has the same meaning as defined above, with a halohydrin derivative represented by the formula (III):

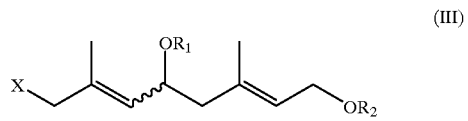

(III)

wherein X represents a halogen atom, and $R_1$ and $R_2$ each represent a protective group of a hydroxyl group, in the presence of a base.

3. The process according to claim 2, wherein the base is an alkyllithium, a Grignard reagent, a hydroxide of an alkali metal, a hydroxide of an alkaline earth metal, a hydride of an alkali metal, a hydride of an alkaline earth metal, an alkoxide of an alkali metal, or an alkoxide of an alkaline earth metal.

4. The process according to claim 2 or 3, wherein the reaction is carried out in the presence of a phase transfer catalyst.

5. The process according to claim 4, wherein the phase transfer catalyst is a quaternary ammonium salt.

6. The process according to claim 5, wherein the quaternary ammonium salt is an ammonium halide containing an alkyl group having 1 to 24 carbon atoms, an aryl group or an alkyl group having 1–24 carbon atoms and an aryl group.

7. A process for producing the ketosulfone derivative of the formula (I) as defined in claim 1, which comprises reacting a sulfone derivative represented by the formula (IV):

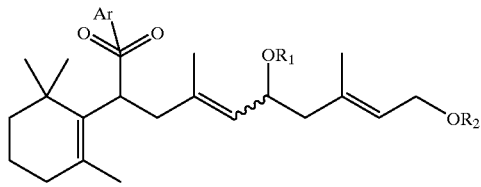
(IV)
wherein Ar is the same as defined in claim 1, and $R_1$ and $R_2$ each represent a protective group of a hydroxyl group, with an oxidizing agent.
8. The process according to claim 7, wherein the oxidizing agent is a salt of chromium or manganese, or an oxide of chromium or manganese.
\* \* \* \* \*